(12) United States Patent
Kessler et al.

(10) Patent No.: US 8,564,316 B2
(45) Date of Patent: Oct. 22, 2013

(54) GEM TESTER

(75) Inventors: Daniel L. Kessler, Dallas, TX (US);
Henry M. Kessler, Dallas, TX (US)

(73) Assignee: Sy Kessler Sales, Inc., Dallas, TX (US)

( * ) Notice: Subject to any disclaimer, the term of this patent is extended or adjusted under 35 U.S.C. 154(b) by 359 days.

(21) Appl. No.: 13/165,053

(22) Filed: Jun. 21, 2011

(65) Prior Publication Data

US 2012/0049836 A1    Mar. 1, 2012

Related U.S. Application Data

(60) Provisional application No. 61/356,943, filed on Jun. 21, 2010.

(51) Int. Cl.
*G01R 27/08*    (2006.01)
(52) U.S. Cl.
USPC .......................................... 324/717; 324/693
(58) Field of Classification Search
USPC ........ 324/71.1, 693, 691, 717, 715, 713, 722, 324/724, 649, 600
See application file for complete search history.

(56) References Cited

U.S. PATENT DOCUMENTS

| | | |
|---|---|---|
| 2,789,430 A | 4/1957 | Sinclaire |
| 4,255,962 A | 3/1981 | Ashman |
| 4,344,315 A | 8/1982 | Moxon et al. |
| 4,364,677 A | 12/1982 | Ashman |
| 4,394,580 A | 7/1983 | Gielisse |
| 4,488,821 A | 12/1984 | Wenckus |
| 5,801,819 A | 9/1998 | Spear et al. |
| 5,883,389 A | 3/1999 | Spear et al. |
| 5,955,735 A | 9/1999 | Coleman |
| 6,265,884 B1 * | 7/2001 | Menashi et al. ............. 324/717 |
| 6,439,766 B1 | 8/2002 | Nelson |
| 7,126,351 B2 | 10/2006 | Claus |
| 7,362,109 B2 * | 4/2008 | Loginov ........................ 324/693 |
| 8,278,906 B2 * | 10/2012 | Loginov et al. .............. 324/71.1 |
| 2012/0007619 A1 * | 1/2012 | Zhu et al. ...................... 324/717 |

* cited by examiner

*Primary Examiner* — Hoai-An D Nguyen
(74) *Attorney, Agent, or Firm* — Scott T. Griggs; Griggs Bergen LLP

(57) ABSTRACT

A gem tester for testing a gem under test and a kit including a horizontal recharging stand are disclosed. In one embodiment of the gem tester, an elongated body has a line-of-sight contour tapering from a bulbous end to a radially deviating frontal nose having a probe extending therefrom. Internal circuitry measures electrical and thermal conductivity of the gem under test in order to identify the type of gem under test and drive a color control signal in response thereto. A luminescent mounting extends about the contact to provide, in response to the control signal, a color indication of the identified gem type.

24 Claims, 7 Drawing Sheets

GEM TESTER

PRIORITY STATEMENT & CROSS-REFERENCE TO RELATED APPLICATIONS

This application claims priority from U.S. Patent Application No. 61/356,943, entitled "Gem Tester" and filed on Jun. 21, 2010, in the names of Kessler et al.; which is hereby incorporated by reference for all purposes.

TECHNICAL FIELD OF THE INVENTION

This invention relates, in general, to the identification of precious diamonds and, in particular, to gem testers for distinguishing gems such as diamond, moissanite, and metals based upon physical conductivity properties.

BACKGROUND OF THE INVENTION

Gemstones such as cubic zirconium and silicon carbide, commonly known as moissanite, have become more readily available and more indistinguishable from real diamonds. As a result, the market is flooded with moissanite which is passed off as diamond. Advances in instruments and techniques are required to authenticate diamonds and prevent fraudulent and mistaken sales.

SUMMARY OF THE INVENTION

It would be advantageous to achieve advances in instruments to authenticate diamonds in order to prevent fraudulent and mistaken sales. It would also be desirable to enable an electro-mechanical solution that would improve operator technique when authenticating diamonds. To better address one or more of these concerns, a gem tester for testing a gem under test and a horizontal recharging stand are disclosed. In one embodiment of the gem tester, an elongated body has a line-of-sight contour tapering from a bulbous end to a radially deviating frontal nose having a probe extending therefrom. Internal circuits measure electrical and thermal conductivity of the gem under test in order to verify or, more generally, identify the type of gem under test and drive a color control signal in response thereto. A luminescent mounting extends about the probe to provide, in response to the control signal, a color indication of the verified or, more generally, identified gem type.

In one embodiment of a gem testing kit, a horizontal recharging stand includes a base having a substantially horizontal support surface and a cavity defining a cradle within the base. The cradle is configured to securely accept the gem tester by way of an inclined support plane, opposing sidewalls, and a backstop. Electrical prongs are exposed at the backstop in order to mate with the recharging contacts when the gem tester is cradled in the horizontal recharging stand. Upon cradling, the gem tester may be recharged. These and other aspects of the invention will be apparent from and elucidated with reference to the embodiment(s) described hereinafter.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which.

DETAILED DESCRIPTION OF THE INVENTION

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention, and do not delimit the scope of the present invention.

Figure 1:
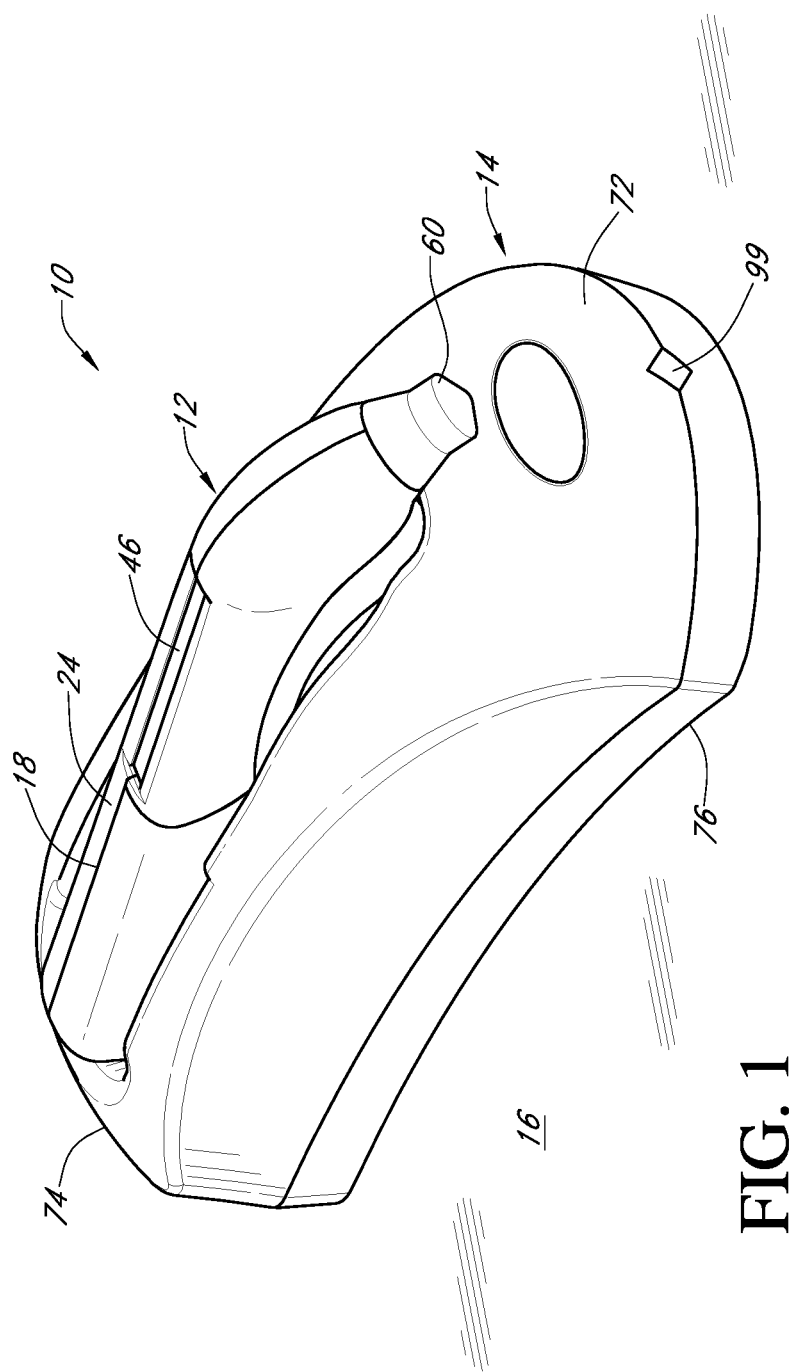
FIG. 1 is a front perspective view of one embodiment of the gem testing kit, which includes a gem tester cradled in a horizontal testing stand.
Figure 2A:
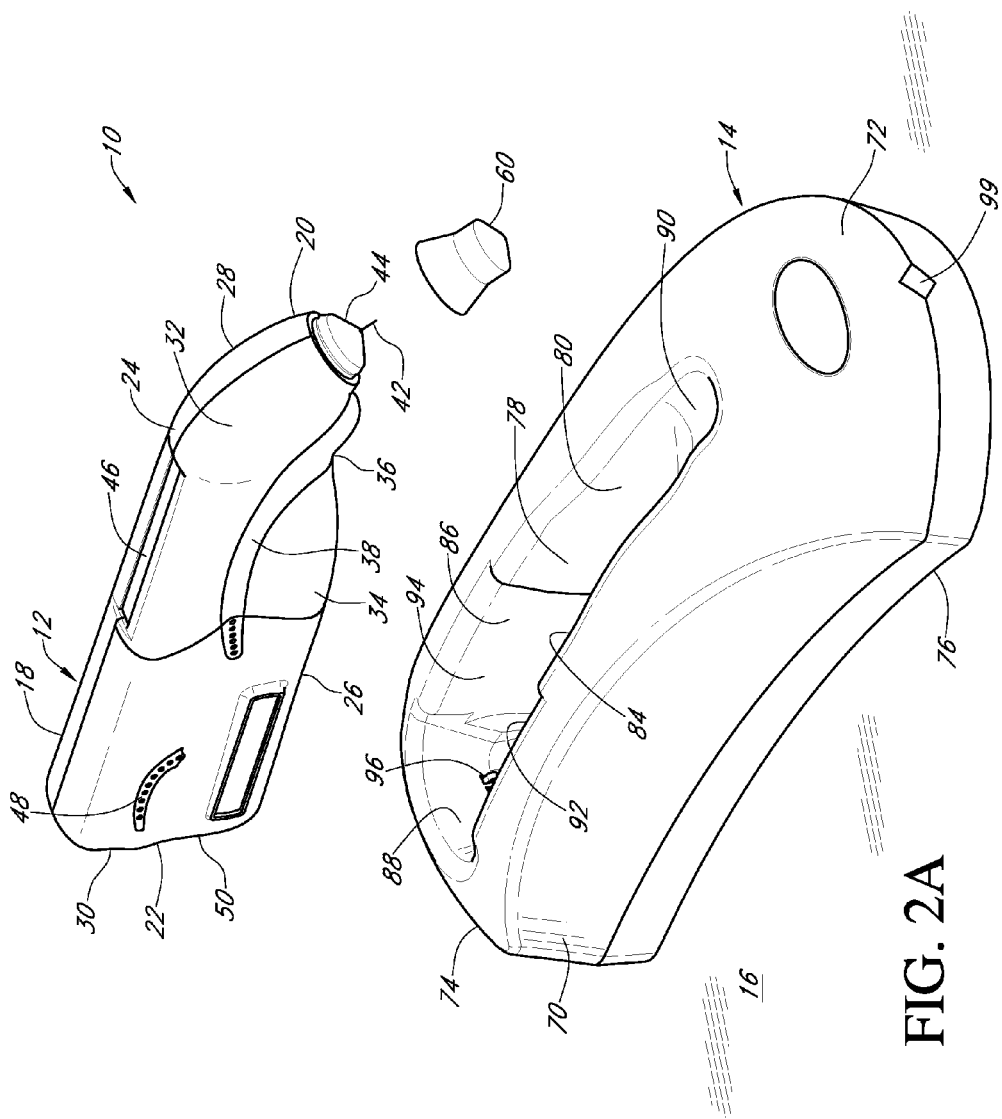
FIG. 2A is a front perspective view of the gem tester of FIG. 1 removed from the horizontal testing stand of FIG. 1.
Figure 2B:
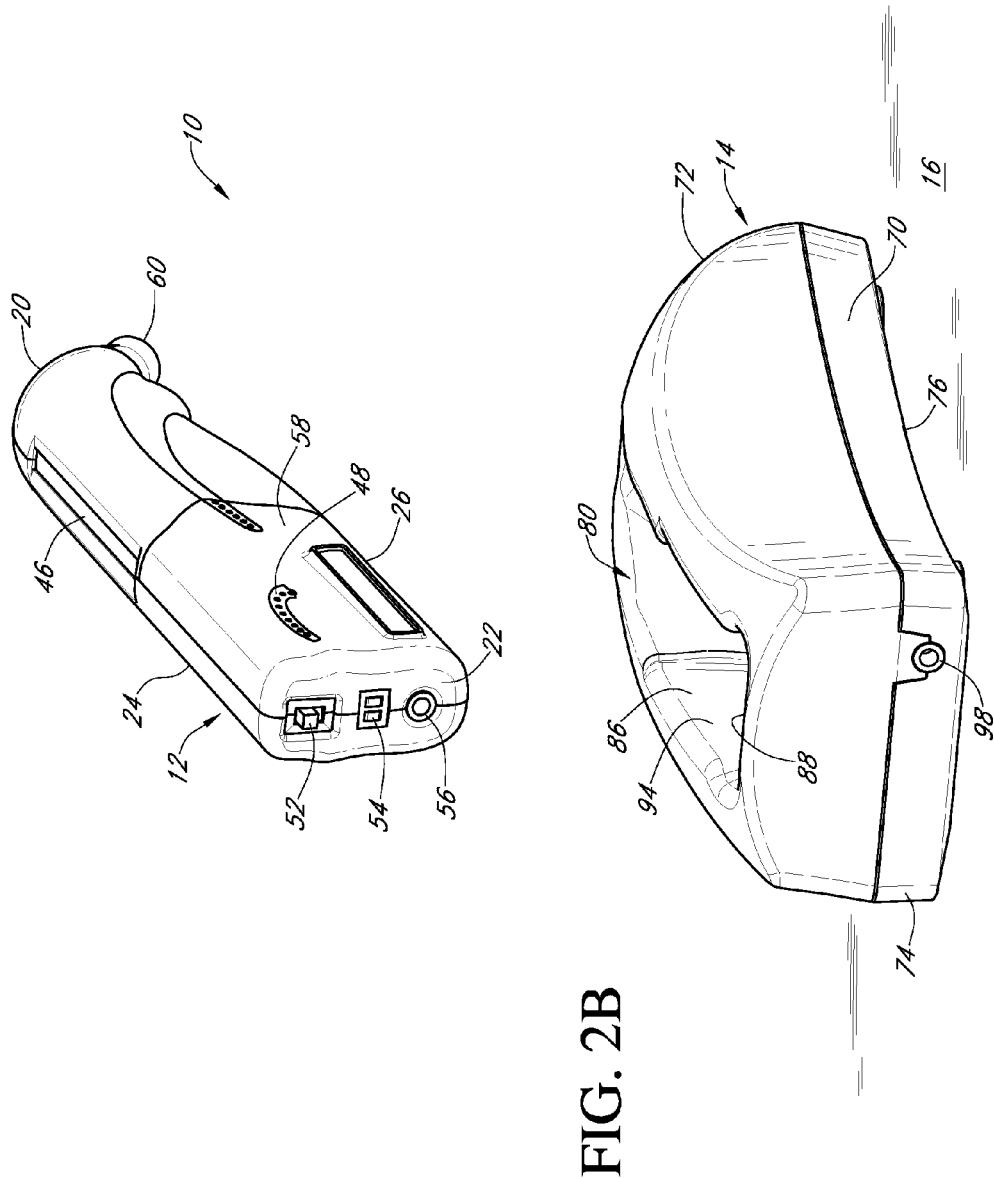
FIG. 2B is a rear perspective view of the gem tester of FIG. 1 removed from the horizontal testing stand of FIG. 1.
Figure 2C:
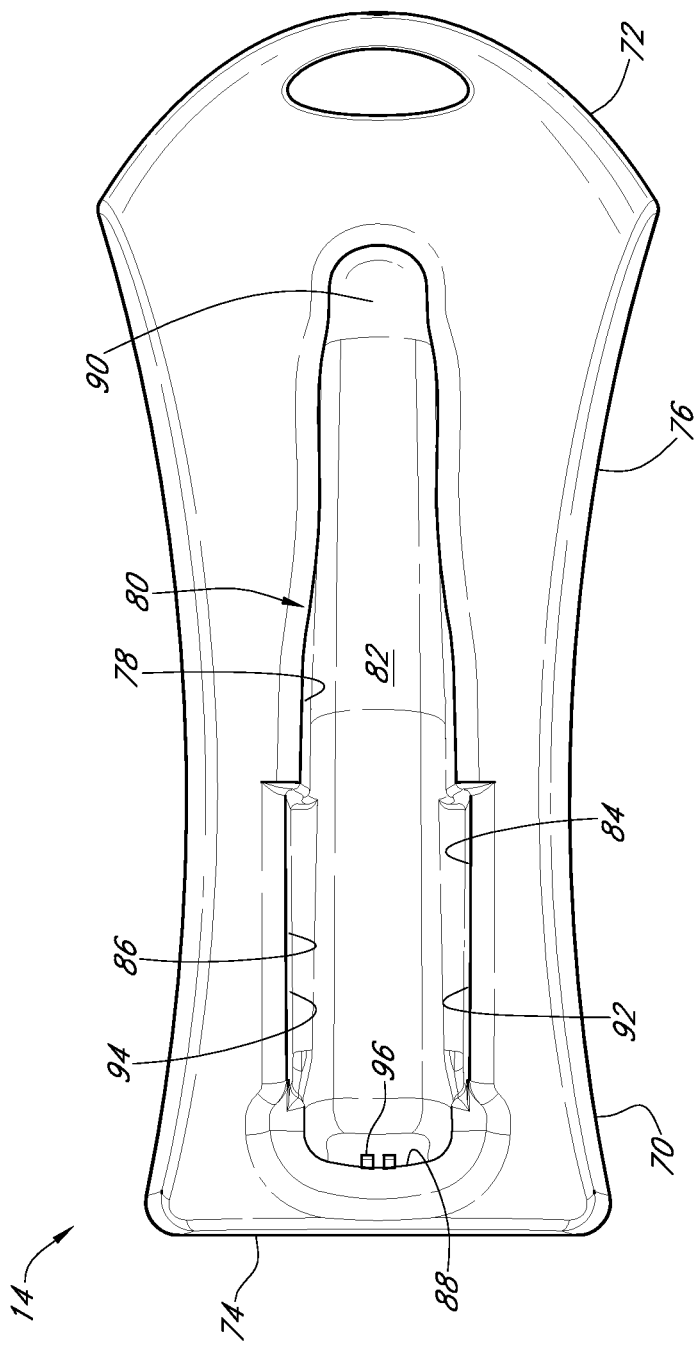
FIG. 2C is a top plan view of the horizontal testing stand of FIG. 1.

Referring initially to FIGS. 1 through 2C, therein is depicted a gem testing kit that is schematically illustrated and generally designated 10. The gem testing kit 10 includes a gem tester 12 shown cradled within a horizontal recharging stand 14, which is depicted resting on surface 16, and removed therefrom. With respect to the gem tester 12, an elongated body 18 includes ends 20, 22 as well as an upper surface 24 and a lower surface 26. As the illustrated embodiment shows, end 20 includes a radially deviating frontal nose 28 and the end 22 includes a bulbous form 30. The elongated body 18 has a tapered contour 32 from the end 22 to the end 24. A tripod contoured surface 34 is proximate to the end 20 and configured to accept a tripod hand grip. More particularly, the tripod contoured surface 34 furnishes a V-shape arcuate portion 36 intersecting respective lateral grip areas 38, 40.

A probe 42 for contacting a gem under test extends from the end 20. In one embodiment, the probe 42 includes a deflectable probe configured to be displaced in response to contact pressure with a gem under test. A luminescent mounting 44 is mounted proximate to the end 20 and, in the illustrated embodiment, extends from the end 20 about the probe 42 to furnish white illuminating light to increase visibility of the probe 42 and gem under test. Additionally, the luminescent mounting 44 provides an indicator light indicative of the test results and gem type (or non-gem type) by way of color.

Display 46, which may be an LED display, is located on the upper surface 24. A speaker 48 is positioned at the end 22 and a battery compartment cover 50 is positioned on the opposite side thereto. The battery cover 50 is slidably releasable to expose a battery compartment for accepting batteries. At end 22, a switch 52 for controlling ON/OFF, recharging contacts 54, and a wall adapter interface 56 are located. With respect to the weight of the weight of the gem tester 12 in one embodiment, a center of mass 58 is proximate the end 22 when the gem tester 12 is batteried. A cone-shaped removable protective cap 60 is releasably secured with a snap-fit engagement to the end 20 to provide protection thereto over the probe 42 and luminescent mounting 44.

The horizontal recharging stand 14 includes a base having a front 72 and a rear 74. A substantially horizontal support surface 76 contacts the surface 16. A cavity 78 defines a cradle 80 within the base 70. As illustrated, in one embodiment, the cradle 80 is configured to accept the gem tester 12. An inclined support plane 82 inclines from the rear 74 toward the front 72 of the horizontal recharging stand 14. Opposing sidewalls 84, 86 run the length of the inclined support plane 82 adjacent to and vertically from the inclined support plane 82. A backstop 88 located near the rear 74 of the inclined support plane 82 intersects the inclined support plane 82 and the opposing sidewalls 84, 86. Further, the inclined support plane 82 includes a tripod support crest 90 which conforms to the V-shape arcuate portion 36 of the tripod contoured surface 34 of the gem tester 12. The side walls 84, 86 include respective indentations 92, 94 conformed to accommodate the shape of the bulbous form 30 of the end 22.

Recharging prongs 96 extend or are exposed at the backstop 88 and are positioned to mate with the recharging contacts 54 of the gem tester 12 when the gem tester 12 is cradled within the horizontal recharging stand 14. A wall adapter interface 98 is located at the rear 74 of the horizontal recharging stand 14. Although not shown in the drawings, the recharging prongs 96 and wall adapter interface 98 are electrically coupled. Additionally, a charging light 99, which displays the status of the recharging proximate the front 72 of the horizontal recharging stand 14 is electrically coupled to the recharging prongs 96 and wall adapter interface 98.

In operation, in a cradled configuration, the recharging stand 14 is located substantially horizontal to the surface 16. The lower surface 26 and bulbous form 30 of the end 22 of the gem tester 12 rest in contact with the sidewalls 84, 86 and the backstop 88. The slope of the inclined support plane 82 causes the end 20 to rest at a higher elevation than the end 22. The tripod support crest 90 supports the V-shape arcuate portion 36 of the tripod contoured surface 34 of the gem tester 12. In the cradled configuration, the recharging contacts 54 touch the recharging prongs 96.

When needed, the gem tester 12 may be easily drawn from the recharging stand 16 between the thumb and index finger. Then, the gem tester 12 may be presented for use by way of a one-hand tripod hand grip whereby the middle finger is placed under the V-shaped arcuate portion 36 and the thumb and forefinger are used to laterally grasp the lateral grip areas 38, 40 of the gem tester 12.

When use is complete, the gem tester 12 may be returned to the recharging stand 14 to the cradled position previously discussed. As mentioned, the center of mass 58 is proximate the end 22 when the gem tester 12 is battered. Therefore, gravity induces the bulbous form 30 of the end 22 to fall into the cradle 80 at the backstop 88. This action results in a circuit being formed between the recharging contacts 54 of the gem tester 12 and the recharging prongs 96 of the recharging stand 14. Once cradled, the gem tester 12 has a low profile wherein the radially deviating frontal nose 28 is at the highest point.

Figure 3A:
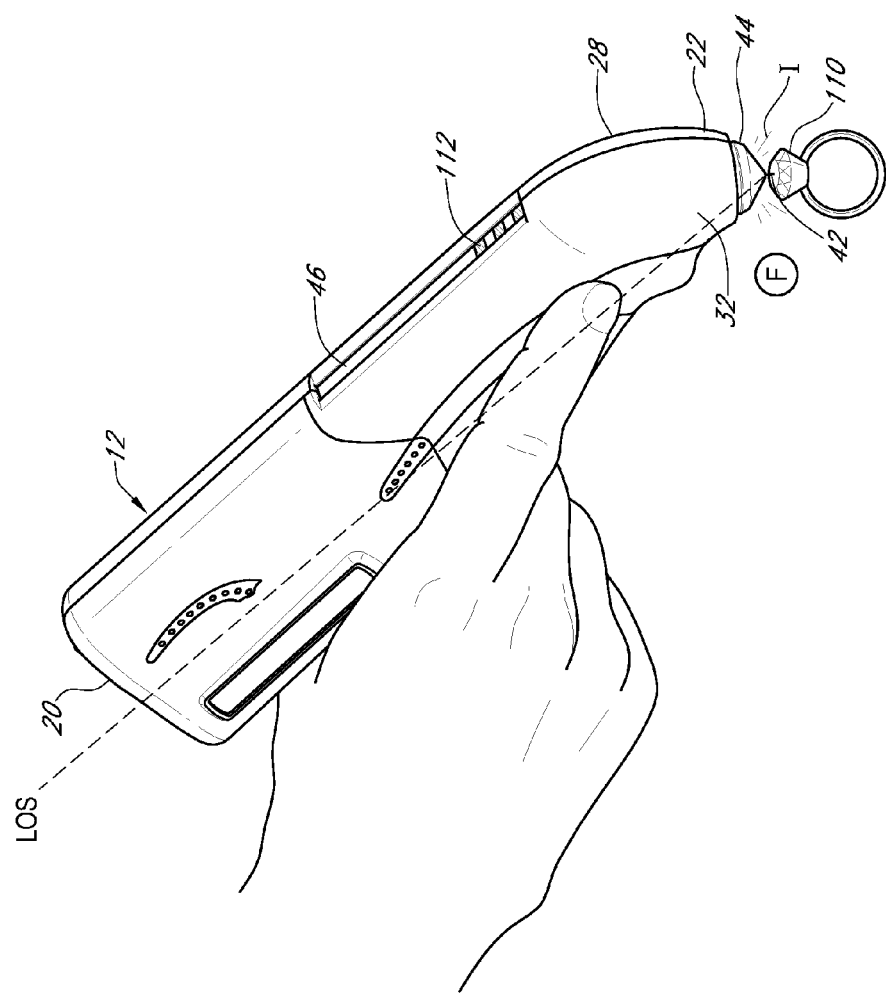
FIG. 3A is side elevation view of the gem tester of FIG. 1 in an operational embodiment testing a gem under test.
Figure 3B:
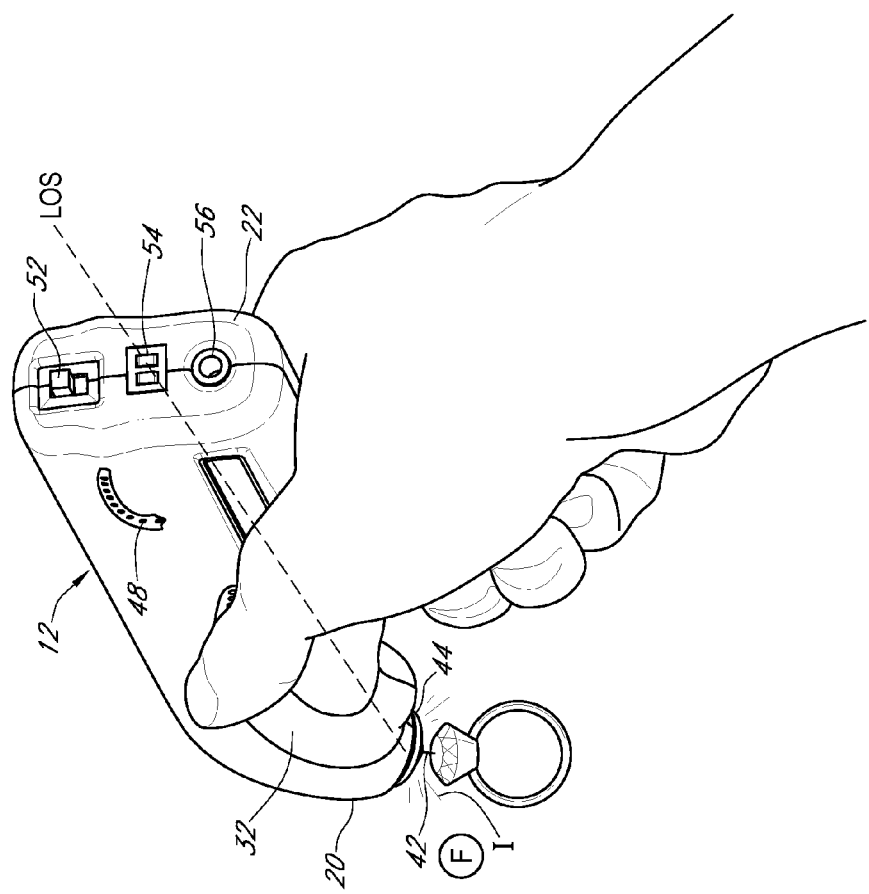
FIG. 3B is a rear elevation view of the gem tester of FIG. 3A in the operational embodiment testing the gem under test.

Referring to FIGS. 3A and 3B, and describing the testing operation of the gem tester 12, the battery compartment cover 50 may be temporarily removed and replaced to install batteries, such as three AAA 1.5 V alkaline batteries. The switch 52 may be toggled to ON to initialize the gem tester. Following a warm-up time, which may be approximately 30 seconds, the gem tester 12 is ready to be used once the cone-shaped protective cap 60 is removed. Using a comfortable grip, the hand of the user holds the gem tester 12. As illustrated, the gem tester 12 may be held with a one-hand tripod hand grip whereby the middle finger is place under the V-shape arcuate portion 36 and the thumb and forefinger are used to laterally grasp the sides of the gem tester 12 at lateral grip areas 38, 40 for handling purposes to maintain control.

Using the one-hand tripod hand grip to comfortably handle the gem tester 12, a gem under test 110 may be tested. The LED display 46, which may depict a bar graph 112, stops blinking and the ready light remains on when the gem tester 12 is ready for use. The user then quickly yet firmly makes contact between the probe 42 and the table of the gem under test 110. If a mounted gem is being tested, care is taken to not touch the setting. Additionally, to ensure test accuracy, the gem under test 110 and the setting should be at room temperature. A gem under test that is overheated due to prolonged exposure to the probe 42 will not test accurately. Contact is maintained for long enough to establish a reading, which in one implementation is one to two seconds.

The reading process makes two measurements: thermal conductivity and electrical conductivity. The thermal conductivity test separates diamond from all known diamond simulants, except moissanite, since diamonds conduct heat significantly greater than all other gemstones, except moissanite. White sapphire is thermally conductive, yet not as conductive as diamond and moissanite and can be therefore easily be separated. Since moissanite conducts electricity in varying degrees and diamonds generally do not conduct electricity, the electrical conductivity test separates the vast majority of moissanite from diamond is the electrical conductivity test. Therefore, based upon readings from the conductivity and electrical tests, the type of gem or metal may be determined.

A line-of-sight contour 32 extends from the end 22 to the end 20 to provide a line-of-sight (LOS). This line-of-sight contour 32 allows the probe 42 and the luminescent mounting 44 to both be visible within the same field of view (F) by an operator. The operator does not have to move his or her eyes between the probe 42 and the luminescent mounting 44 during operation and determination of gem type. The operator does not want to shift his eyes away from the probe 42 to view any indicator. Often, the probe 42 is contacting a very small area and a slight movement of the probe 42 in any direction place the probe 42 into contact with a different surface resulting in a misleading reading.

Initially, in one implementation, the luminescent mounting may provide a white working light (I) in the field of view (F) that is visible to the operator along the line-of-sight (LOS) along the line-of-sight contour 32. The working light illuminates the gem under test 110 to give the operator extra visibility to ensure a proper probe contact. Based upon readings from the conductivity and electrical tests, the type of gem or metal may be determined by the gem tester 12. Following the determination, the luminescent mounting 44 provides a color indication (I) which is in the field of view (F) and visible along the line-of-sight (LOS) along the line-of-sight contour 32. For example, with respect to the indication (I), a green light (G) may indicate diamond, a blue light (B) may indicate moissanite, and a yellow light (Y) may indicate metal.

Figure 4:
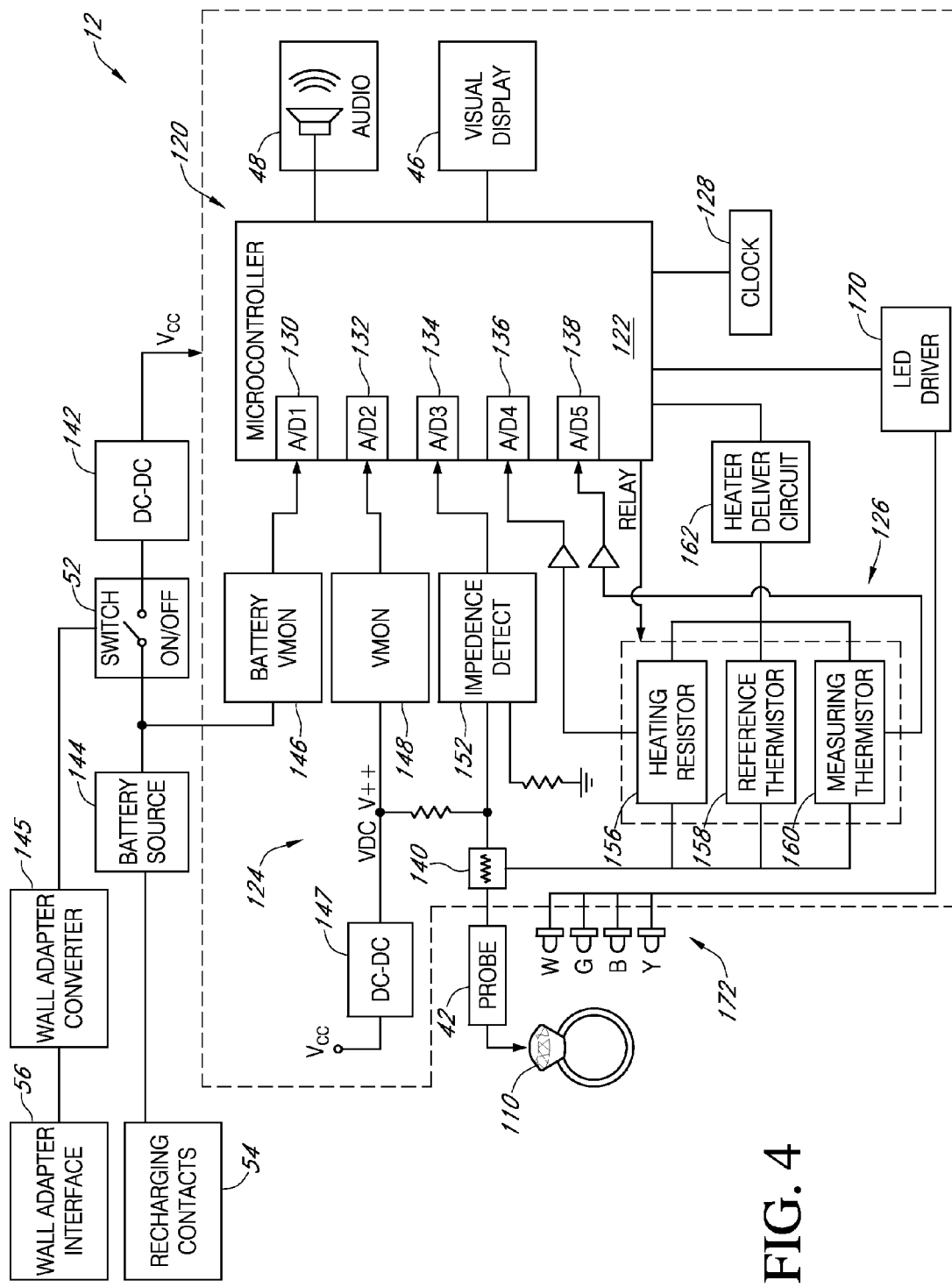
FIG. 4 is a schematic block diagram of one embodiment of the gem tester.

FIG. 4 depicts one embodiment of the gem tester 12 in further detail. A circuit portion 120, including the micocontroller, which may be a microprocessor 122, is located communicatively with circuit portions 124, 126 and configured to determine or more generally identify verified—or, more generally, identified—type and drive a color control signal in response thereto. The identified type being selected from a plurality of gem types including at least three materials. Additionally, the identified type may be a non-gem type, such as metal. More particularly, at the center of the circuit portion 120, the microprocessor 122, operating under the frequency source of a clock 128, processes a number of analog voltages at inputs 130, 132, 134, 136, 138 to produce a number of outputs (discussed below) indicative of whether a measurement for the gem under test is within a specific range indicating that the gem under test is diamond, moissanite, or other metal.

The switch 52, which may be a single pole single throw mechanical switch, controls the ON/OFF state of gem tester 12 and the application of voltage to DC-DC converter 142. A voltage source may be a battery source 144, regular or rechargeable, or wall power provided by a wall adapter converter 145 and wall adapter interface 56. The low voltage DC-DC converter 142 converts the battery source 144 or voltage supplied by the wall adapter converter 145 to an acceptable voltage for powering analog and digital circuitry. A battery voltage monitor 146 is provided to detect a low voltage condition in the battery source and communicate this information to the microprocessor 122 via the input 132. A DC-DC converter 147 and a monitor circuit 148 are designed to condition the signal for processing within the microprocessor 122. If low voltage condition is detected, the audio speaker 48 or the visual display 46, both of which are connected to the microprocessor 122, may provide an indication of faulty voltage while testing is temporarily suspended by the gem tester 12. In particular, the microprocessor 122 discontinues gem testing when the voltage source input is below a certain pre-determined threshold.

The circuit portion 124 is electrically coupled to the probe 42, which is shown as a deflectable probe having a spring 140 thereat, to measure electrical conductivity of the gem under test 110. More particularly, the circuit portion 124 includes electrical components 150, including the DC-DC converter 147, the voltage monitor 148, and an impedance detector 152, for applying and sampling a voltage across the gem under test 110. The electrical components 150 successively sample the voltage across the gem under test 110 to provide data for determining a gem type based upon a predetermined number of samples exceeding a threshold voltage. As shown, the voltage monitor is coupled to the microprocessor 122 by the input 132 and the impedance detector 152 is coupled to the microprocessor by the input 134.

The circuit portion 126 is thermally coupled to the probe 42 to measure thermal conductivity of the gem under test 110. Heating components 154, including a heating resistor 156, reference thermistor 158, and a measuring thermistor 160, heat the probe 42 and monitor the temperature of the heated probe 42. The heater deliver circuit 162 is located between the microprocessor 122 and the heating resistor 156, the reference thermistor 158, and the measuring thermistor 160. As depicted, the heating resistor 156 is connected to the microprocessor 122 by the input 136 and an amplifier. Similarly, the measuring thermistor 160 is connected to the microprocessor 122 by the input 138 and an amplifier.

An LED driver 170 controls LEDs 172 in response to receiving signals from the microprocessor 172. In one implementation, one LED provides a white working light (W) and the other LEDs provide indication lights that indicate the composition of the gem under test. For example, a green light (G) may indicate diamond, a blue light (B) may indicate moissanite, and a yellow light (Y) may indicate metal. That is, in the illustrated embodiment, the LED driver 170 and LEDs 172 provide a white working light as well as at least three colors of light, which are indicators of three separate types of gem or non-gem materials.

It should be appreciated that the circuit design and architecture depicted in FIG. 4 is only exemplary and illustrative. Other designs and architectures are within the teachings presented herein. By way of example, the circuit portion 124 configured to measure electrical conductivity and the circuit portion 126 configured to measure thermal conductivity may be combined. By way of further example, illumination or indicators other than LEDs may be utilized to provide working light and color indicators.

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. A gem tester for testing a gem under test, the gem tester comprising:
    an elongated body having a first end and a second end;
    a probe extending from the first end of the elongated body;
    a first circuit portion located within the elongated body, the first circuit portion being electrically coupled to the probe to measure electrical conductivity of the gem under test;
    a second circuit portion located within the elongated body, the second circuit portion being thermally coupled to the probe to measure thermal conductivity of the gem under test;
    a third circuit portion located within the elongated body communicatively with the first and second circuit portions, the third circuit portion configured to determine identified type and drive a color control signal in response thereto, the identified type being selected from a plurality of gem types including at least three materials;
    a luminescent mounting extending from the first end communicatively with the third circuit portion, the luminescent mounting providing a plurality of colors corresponding to the plurality of gem types, the luminescent mounting lighting one of the plurality of colors in response to receiving the color control signal; and
    a line-of-sight contour extending from the second end of the elongated body to the first end of the body, including the luminescent mounting to the probe.

2. The gem tester as recited in claim 1, wherein the elongated body further comprises:
    the first end having a radially deviating frontal nose;
    the second end having a bulbous form;
    the elongated body being tapered from the first end to the second end; and
    a center of mass being proximate the second end when the gem tester is batteried.

3. The gem tester as recited in claim 1, wherein the elongated body further comprises a tripod contoured surface proximate to the first end, the tripod contoured surface configured to accept a tripod hand grip.

4. The gem tester as recited in claim 1, wherein the probe further comprises a deflectable probe configured to be displaced in response to contact pressure.

5. The gem tester as recited in claim 1, wherein the first circuit portion further comprises electrical components for applying a voltage across the gem under test, the electrical components successively sampling the voltage across the gem under test to provide data for determining a gem type based upon a predetermined number of samples exceeding a threshold voltage.

6. The gem tester as recited in claim 1, wherein the second circuit portion further comprises heating components for heating the probe and monitoring the temperature of the heated probe.

7. The gem tester as recited in claim 1, wherein the third circuit portion further comprises a microprocessor.

8. The gem tester as recited in claim 1, wherein the first, second, and third circuit portions are at least partially integrated.

9. The gem tester as recited in claim 1, wherein the luminescent mounting further comprises white light source for illuminating the gem under test.

10. The gem tester as recited in claim 1, wherein the luminescent mounting further comprises green, red, and blue colors.

11. The gem tester as recited in claim 1, wherein the gem tester identifies diamond, metal, and moissanite.

12. The gem tester as recited in claim 1, further comprising a releasable cap having a snap-fit engagement about the probe.

13. A gem tester for testing a gem under test, the gem tester comprising:
an elongated body having a first end and a second end;
a probe extending from the first end of the elongated body;
means for measuring electrical conductivity of the gem under test communicatively disposed with the probe;
means for measuring thermal conductivity of the gem under test communicatively disposed with the probe;
a circuit portion located within the elongated body communicatively with the means for measuring electrical conductivity and means for measuring thermal conductivity, the circuit portion configured to determine identified type and drive a color control signal in response thereto, the identified type being selected from a plurality of gem types including at least three materials;
means for providing, in response to receiving the color control signal, a plurality of colors corresponding to the plurality of gem types; and
a line-of-sight contour extending from the second end of the elongated body to the first end of the body to the luminescent mounting to the probe.

14. The gem tester as recited in claim 13, wherein the means for measuring electrical conductivity and the means for measuring thermal conductivity are at least partially integrated.

15. The gem tester as recited in claim 13, wherein the means for providing a plurality of colors further comprises means for providing green, red, and blue colors.

16. The gem tester as recited in claim 13, wherein the gem tester identifies diamond, metal, and moissanite.

17. A gem testing kit, comprising, in combination:
a gem tester comprising:
an elongated body having a line-of-sight contour tapering from a bulbous end to a radially deviating frontal nose having a probe extending therefrom,
a center of mass proximate the bulbous end when the gem tester is batteried,
recharging contacts are exposed at the bulbous end,
an internal circuit coupled to the contact and the recharging contacts, the internal circuit configured to measure electrical and thermal conductivity of the gem under test in order to identify the type of gem under test and drive a color control signal in response thereto, and
a luminescent mounting extending from the elongated body, the luminescent mounting configured to provide, in response to the control signal, a color indication of the identified gem type; and
a horizontal recharging stand comprising:
a base having a substantially horizontal support surface,
a cavity defining a cradle within the base, the cradle configured to accept the gem tester, the cradle including an inclined support plane, opposing sidewalls and a backstop, and
recharging prongs are exposed at the backstop, the electrical prongs being positioned to mate with the recharging contacts when the gem tester is cradled within the horizontal recharging stand.

18. The gem testing kit as recited in claim 17, wherein the elongated body further comprises a tripod contoured surface proximate to the a radially deviating frontal nose, the tripod contoured surface configured to accept a tripod hand grip.

19. The gem testing kit as recited in claim 17, wherein the inclined support plane intersects a tripod support crest, the tripod support crest conforming to the shape of a lower portion of the tripod contoured surface.

20. The gem testing kit as recited in claim 17, wherein the side walls further comprise respective indentations conformed to accommodate the shape of the bulbous end.

21. A gem tester for testing a gem under test, the gem tester comprising:
an elongated body having a first end and a second end;
a probe extending from the first end of the elongated body;
a first circuit portion located within the elongated body, the first circuit portion being electrically coupled to the probe to measure electrical conductivity of the gem under test;
a second circuit portion located within the elongated body, the second circuit portion being thermally coupled to the probe to measure thermal conductivity of the gem under test;
a third circuit portion located within the elongated body communicatively with the first and second circuit portions, the third circuit portion configured to determine identified type and drive a color control signal in response thereto, the identified type being selected from a plurality of gem types including at least three materials;
a luminescent mounting mounted proximate to the first end and communicatively with the third circuit portion, the luminescent mounting providing a plurality of colors corresponding to the plurality of gem types, the luminescent mounting lighting one of the plurality of colors in response to receiving the color control signal; and
a line-of-sight contour extending from the second end of the elongated body to the first end of the body, including the luminescent mounting to the probe.

22. The gem tester as recited in claim 21, wherein the elongated body further comprises:
the first end having a radially deviating frontal nose;
the second end having a bulbous form;
the elongated body being tapered from the first end to the second end; and
a center of mass being proximate the second end when the gem tester is batteried.

23. A gem tester for testing a gem under test, the gem tester comprising:
a body having a line-of-sight contour tapering from a bulbous end to a radially deviating frontal nose having a probe extending therefrom;
a center of mass proximate the bulbous end when the gem tester is batteried;
recharging contacts exposed at the bulbous end; and
an internal circuit coupled to the contact and the recharging contacts, the internal circuit configured to measure at least one of electrical and thermal conductivity of the gem under test in order to identify the type of gem under test and drive a color control signal in response thereto; and a luminescent mounting extending from the body, the luminescent mounting configured to provide, in response to the control signal, a color indication of the identified gem type.

24. A gem tester for testing a gem under test, the gem tester comprising:

a body having an end;

a probe extending from the end of the body;

a first circuit portion located within the body, the first circuit portion being electrically coupled to the probe to measure electrical conductivity of the gem under test;

a second circuit portion located within the body, the second circuit portion being thermally coupled to the probe to measure thermal conductivity of the gem under test;

a third circuit portion located within the elongated body communicatively with the first and second circuit portions, the third circuit portion configured to determine identified type and drive a color control signal in response thereto, the identified type being selected from a plurality of gem types including at least three materials; and a luminescent mounting extending from the end communicatively with the third circuit portion, the luminescent mounting providing a plurality of colors corresponding to the plurality of gem types, the luminescent mounting lighting one of the plurality of colors in response to receiving the color control signal.

* * * * *